United States Patent [19]

Mowrey et al.

[11] 4,168,170

[45] Sep. 18, 1979

[54] DRY HEAT-ACTIVATED BLEACHING OF SILVER IMAGES

[75] Inventors: Rowland G. Mowrey; Edwin N. Oftedahl, both of Rochester, N.Y.

[73] Assignee: Eastman Kodak Company, Rochester, N.Y.

[21] Appl. No.: 878,979

[22] Filed: Feb. 17, 1978

Related U.S. Application Data

[63] Continuation-in-part of Ser. No. 662,403, Mar. 1, 1976, abandoned.

[51] Int. Cl.$^2$ .................. G03C 7/00; G03C 1/76; G03C 1/02
[52] U.S. Cl. .................................. 96/53; 96/73; 96/114.1; 96/50 R; 96/66 T
[58] Field of Search .................. 96/50, 76 R, 53.73, 96/114.1, 66 T; 428/480, 483, 199; 427/145; 526/2, 3, 5

[56] References Cited

U.S. PATENT DOCUMENTS

| | | | |
|---|---|---|---|
| 2,624,725 | 1/1953 | Bjorksten et al. | 526/2 |
| 3,347,675 | 10/1967 | Henn et al. | 96/61 |
| 3,414,411 | 12/1968 | Michel et al. | 96/53 |
| 3,493,372 | 2/1970 | Gompf et al. | 96/73 |
| 3,647,440 | 3/1972 | Rasch | 96/76 R |
| 3,708,300 | 1/1973 | Luckey | 96/73 |
| 3,826,653 | 7/1974 | Jacobs | 96/50 |
| 3,874,895 | 4/1975 | Hayashi et al. | 427/145 |
| 3,904,418 | 9/1975 | Mowrey et al. | 96/73 |
| 3,930,859 | 1/1976 | Corrigan | 96/50 R |

*Primary Examiner*—Mary F. Kelley
*Attorney, Agent, or Firm*—Richard E. Knapp

[57] ABSTRACT

A dry, activator sheet for a dry, thermal silver dye-bleach process, in the absence of a silver dye-bleach catalyst, comprises a support having thereon a nonvolatile, diffusible acid and a non-hydrolyzable polymeric vehicle having an effective pH up to 4.0 and a melting point lower than 200° C. The activator sheet is useful to bleach a silver image containing a bleachable dye.

28 Claims, No Drawings

DRY HEAT-ACTIVATED BLEACHING OF SILVER IMAGES

This is a continuation-in-part application of U.S. Ser. No. 662,403 of R. G. Mowrey and E. N. Oftedahl, filed Mar. 1, 1976 now abandoned.

This invention relates to dry, activator sheets for use in bleaching photographic elements containing a silver image and a bleachable dye and to photographic elements and processes for bleaching silver images and dyes.

Many methods to produce positive color images with photographic silver halide materials have been described in the art. Those which are successfully employed in today's color photographic art include the silver dye-bleach process, as described, for example, in J. S. Friedman, *History of Color Photography*, (1944) pp. 405–429 and A. Meyer, *The Journal of Photographic Science*, Vol. 13, 90–97 (1965) and *"The Theory of the Photographic Process"*, edited by T. H. James, Fourth Edition, 1977, pages 363–366; the color imaging process, as described in U.S. Pat. No. 2,252,718; and reversal processes which utilize the color development of photographic silver halide elements containing incorporated color-forming couplers, as described, for example, in U.S. Pat. Nos. 2,944,900; 2,984,567 and 3,189,452. In each of these processes, however, lengthy solution processing techniques are required which rely heavily on precision control and sophisticated techniques in order to produce color photographic images of high quality.

The silver dye-bleach process involves developing a silver image in an exposed silver halide emulsion containing bleachable dye, and subsequently bleaching the dye in those areas where the silver has been developed. All the silver ion is removed or rendered transparent and insensitive to light by the bleach action, leaving a positive dye image in the areas where no metallic silver was present.

In most color photographic processes utilizing the above silver dye-bleach system, it has been necessary to subject the exposed film to a large number of processing baths to achieve the discernable image. The exposed element is first developed with a black-and-white developer solution to produce a metallic silver image containing overall dye and then subjected to a strongly acidic dye bleach bath which decolorizes the dye in just those areas where the developed silver is present. The residual silver and silver halide are then removed in a subsequent bleach and fix bath and a direct-positive color image is obtained.

Photothermographic elements, i.e., photographic elements which produce a silver image upon imagewise exposure and then heat development, are described, for example, in Evans and McLaen U.S. Pat. No. 3,801,321 issued Apr. 2, 1974; Sullivan, Cole and Humphlett U.S. Pat. No. 3,785,830 issued Jan. 15, 1974; and Haist et al U.S. Pat. Nos. 3,301,678 and 3,531,285. These elements are particularly desirable in that an image can be produced by a dry process.

Michel et al, U.S. Pat. No. 3,414,411, issued Dec. 3, 1968, discloses an "in-camera" type system employing a photographic element comprising a support having thereon a silver halide emulsion containing the salt of an acid and a developed silver image having in association therewith a bleachable dye, or dye precursor. The exposed emulsion is contacted with a viscous alkaline processing solution and with a web having an acidic substituent which is capable of exchanging hydrogen ion with the cation of the salt of an acid which is present in the emulsion to lower the pH of the emulsion to a level at which imagewise bleaching of the dye in areas of metallic silver and in the presence of a silver complexing agent proceeds. The dye bleaching is described as being conducted in the presence of a catalyst and the web is delaminated to uncover the image.

The processing solution of Michel et al, U.S. Pat. No. 3,414,411, however, requires the use of salts which upon drying render the coating translucent or substantially opaque due to crystallization and the web must be delaminated from the element for viewing purposes. The acid used in the processing web is non-diffusible and immobile. Thus, in order to bleach the silver metal, ion exchange must take place and the web must be peeled apart from the element.

The use of conventional dye bleach solutions is in some ways undesirable in that it is difficult to control the composition of the solution and the process is time consuming.

It has thus been desirable to provide a photographic, and preferably photothermographic, dye bleach process which is dry, stable and does not require removing the bleaching web to produce a positive color image.

SUMMARY OF THE INVENTION

It has been found according to the invention that an element comprising a silver image and at least one overall bleachable dye can provide a positive, dye image in the absence of solutions, and in the absence of a silver dye-bleach catalyst, by contacting the element at moderately elevated temperatures, e.g., about 50° C. to about 150° C., with a dry, activator sheet comprising a support having thereon a layer or layers comprising a nonvolatile, diffusible acid and a non-hydrolyzable polymeric vehicle wherein the layer has an effective pH up to 4.0 and is solid up to at least about 50° C. with a melting point lower than 200° C.

In one embodiment of the invention, a dry, activator sheet for a dry, thermal silver dye-bleach process, in the absence of a silver dye-bleach catalyst, comprises a support having thereon, a layer or layers comprising
  (a) a nonvolatile, diffusible acid selected from the group consisting of nonvolatile, diffusible mineral acids and organic acids containing up to 10 carbon atoms, and
  (b) a non-hydrolyzable polymeric vehicle, wherein said layer or layers has an effective pH of up to 4.0 and is solid up to at least about 50° C. with a melting point lower than 200° C.

In another embodiment, this invention also relates to a process of dye bleaching a photographic element comprising a silver image in association with a bleachable dye by contacting the image at moderately elevated temperatures, in the absence of a silver dye-bleach catalyst, with a dry, activator layer comprising
  (a) a nonvolatile, diffusible acid selected from the group consisting of nonvolatile, diffusible mineral acids and organic acids containing up to 10 carbon atoms, and
  (b) a non-hydrolyzable polymeric vehicle wherein said layer has a pH of up to 4.0 and is solid up to at least 50° C. with a melting point lower than 200° C.

In still a further embodiment a dry, photographic element comprises, in the absence of a silver dye-bleach catalyst, a support having thereon a first layer containing a silver metal image and a uniformly distributed (throughout the layer) bleachable dye and laminated to the first layer a transparent second layer comprising
  (a) a nonvolatile, diffusible acid selected from the group consisting of nonvolatile, diffusible mineral acids and organic acids containing up to 10 carbon atoms, and
  (b) a non-hydrolyzable polymeric vehicle wherein said second layer has a pH of up to 4.0 and is solid up to at least 50° C. with a melting point lower than 200° C.

The activator sheet described herein is stable in the dry condition and can be kept on a shelf for long periods of time prior to use.

DETAILED DESCRIPTION OF THE INVENTION

The dry, activator sheet useful to bleach a silver image in association with a bleachable dye, in the absence of a silver dye-bleach catalyst, comprises a support having thereon a layer or layers comprising
  (a) a nonvolatile, diffusible acid selected from the group consisting of nonvolatile, diffusible mineral acids and organic acids containing up to 10 carbon atoms, and
  (b) a non-hydrolyzable polymeric vehicle wherein said layer or layers has a pH of up to 4.0 and is solid up to at least 50° C. with a melting point lower than 200° C.

The term "dry" as used herein is intended to refer to materials that are dry to the touch. A dry activator sheet, for example, is dry to the touch as used herein. The activator sheet according to the invention can contain a concentration of atmospheric moisture which does not adversely effect the desired dye bleach process. Also the described photographic elements can contain a small concentration of moisture, but are dry to the touch. Before processing, the activator sheet, as described, can contain water of hydration or a concentration of water that does not adversely affect the desired properties of the activator sheet. But, if water is present, it should be removed prior to processing, such as by preheating.

The support for the dry, activator sheet or web can be any material which retains dimensional stability at bleaching temperatures. Example of suitable supports are paper, polyolefins such as polyethylene or polypropylene, polycarbonate, high temperature-resistant film supports such as supports from 1,1,3-trimethyl-5-carboxy-3-(p-carboxyphenyl)indan polymers, cellulose acetate butyrate, polyethylene terephthalate, and the like. The preferred support materials are those which are transparent so that the positive color image can be viewed through the activator sheet.

The support has thereon, either in a layer or layers, the nonvolatile, diffusible acid and the polymeric vehicle. The support and layer or layers containing the above substituents can also be separated by an intermediate layer, such as a timing layer, such as a $TiO_2$ layer, which allows the silver image to be heat developed and bleached in a single heating step, and wherein the timing layer allows the development of the silver image prior to the bleaching by the activator sheet.

The acid used must be nonvolatile to avoid release of undesired materials and must be mobile and diffusible in the photographic laminate comprising the described activator sheet and the photographic element so that the silver image can be effectively bleached in a short period of time. The acid can be selected from the group consisting of nonvolatile, diffusible mineral acids and organic acids containing up to 10 carbon atoms. Each of these acids is useful providing that the processing temperature is lower than that which can vaporize the acid from the described sheet, but high enough to allow migration of the acid to the photographic element.

Nonvolatile, mineral acids useful herein include sulfuric acid, sulfamic acid, phosphoric acid, and the like.

Examples of nonvolatile, diffusible organic acids useful herein are those acids containing up to 10 carbon atoms including carboxylic acids such as citric acid, acetic acid and other acids such as p-toluenesulfonic acid, phenylphosphonic acid, phenylphosphoric acid, phenylphosphinic acid, benzenesulfonic acid, p-toluene sulfinic acid, and the like. Para-toluenesulfonic acid is especially useful.

It is important that the described mineral acids and organic acids be nonvolatile to help avoid release of undesired products from the activator sheet or element according to the invention, especially at processing temperatures. The term "nonvolatile" as used herein is intended to mean that no significant concentration of acid, as described, is vaporized from the activator sheet or element according to the invention at processing temperature. For example, para-toluenesulfonic acid is a nonvolatile acid within the invention because no significant bubble or other defects arise from vaporization of this acid according to the invention at processing temperature. Nonvolatile acids useful in the practice of the invention can also be selected based, in part, on the boiling point of the acids provided in, for instance, Tables of Physical Constants of Inorganic and Organic Compounds, *Handbook of Chemistry and Physics*, 57th Edition, CRC Press, 1976–1977.

It is critical that the acid be diffusible. By the term "diffusible acids" it is meant that the acids in themselves are mobile within the photographic laminant at the processing temperatures employed or they can be rendered mobile by the use of a suitable thermal solvent.

The acid incorporated in the activator sheet is generally strongly acidic and/or present in sufficient proportions to provide an effective pH of 4.0 or lower in the layer or layers on the support. Acids which are unable even at large proportions to reduce the pH in the layer or layers at a value below 4.0 would not be suitable for use according to the invention.

The term "effective pH up to 4.0" is intended herein to mean that the concentration of the described nonvolatile, diffusible acid in the activator sheet, as described, is sufficient, at the described processing temperature, to enable the desired silver dye-bleach reaction according to the invention to occur in the absence of a silver dye-bleach catalyst. Each of the examples that illustrate the invention in the folowing description have an effective pH up to 4.0. The desired pH within the activator sheet can be determined by pH measurement techniques known in the chemical analytical art. For instance, a certain size sample of the activator sheet, as described, can be immersed in a certain quantity of water and the pH measured with a pH measuring apparatus known in the chemical art. In situations in which this is not convenient or suitable, a simple, acid concentration, test series can be carried out in which the concentration of nonvolatile, diffusible acid is varied in the activator sheet according to the invention until the desired concentration is reached which produces the desired silver dye-bleach reaction at processing temperature. Also, another method which can be useful comprises placing a drop of water on the surface of the activator sheet according to the invention and measuring the pH at the surface of the sheet with a known pH measuring apparatus with an electrode designed to measure surface pH. In many instances, this latter method is most convenient.

The polymeric vehicle useful in this invention is a film-forming polymeric material containing organic residues which are non-hydrolyzable or slow to hydrolyze such as poly(vinyl alcohol), poly(acrylic acid), poly(styrene sulfonic acid), poly(vinylpyrrolidone), poly(ethylene oxide), and the like. It is critical that the vehicle be non-hydrolyzable or slow to hydrolyze because hydrolyzable vehicles such as gelatin compete for hydrogen ions and become hydrolyzed and denatured by the presence of the acid in the layer. The resulting layers then would be effective for only a short period of time after coating.

By the term "non-hydrolyzable vehicle" it is meant that a coating containing said vehicle and said diffusible acid, when kept at room temperature, i.e., about 19° C., 50% relative humidity for about 4 weeks, shows no appreciable loss in activity due to pH changes caused by, for example, transesterification or transamidation reactions.

Examples of non-hydrolyzable vehicles useful herein are sulfonated polystyrene, poly(acrylic acid), poly(acrylamide), poly(vinyl alcohol), poly(vinylpyrrolidone), poly(ethylene oxide), and active methylene containing polymers such as copolymers of acrylamide and ethyl 5-(m- and p-vinylphenyl)-3-oxo-pentanoate, copolymers of acrylamide and 6-(m- and p-vinylbenzyl)-2,4-hexanedione and the like. Poly(vinylpyrrolidone) is especially useful.

A silver halide complexing agent generally known in the art as a fixing agent must be present in either the activator sheet of the invention or it must be incorporated in the photographic element employed. As used herein, the term "complexing agent" refers to compounds which either (1) dissolve and remove silver ion from the emulsion layer or (2) are stabilizing compounds which react with the silver ion to render it insensitive to light and transparent.

The complexing agent employed herein in one form can be that of a conventional silver halide solvent. Silver halide solvents are defined as compounds which, when employed in an aqueous solution (60° C.), are capable of dissolving more than ten times the amount (by weight) of silver halide which can be dissolved in water at 60° C.

Typical useful silver halide solvents include water-soluble thiosulfates (e.g., sodium thiosulfate, potassium thiosulfate, ammonium thiosulfate, and the like), thiourea, ethylene-thiourea, a water-soluble thiocyanate (e.g., sodium thiocyanate, potassium thiocyanate and ammonium thiocyanate), and a water-soluble sulfur-containing dibasic acid. Water-soluble diols used to advantage include those having the formula: $HO(CH_2CH_2Z)_pCH_2CH_2OH$, wherein p is an integer of from 2 to 13, and Z represents oxygen or sulfur atoms such that at least one third of the Z atoms are sulfur and there are at least two consecutive Z's in the structure of the compound which are sulfur atoms. The diols advantageously used are also included in compounds having the formula: $HO(-CH_2CH_2X)_{c-1}(-CH_2CH_2X^1)_{d-1}(-CH_2CH_2X)_{e-1}(-CH_2CH_2X^1)_{f-1}(CH_2CH_2X)_{g-1}-CH_2CH_2OH$, wherein X and $X^1$ represent oxygen or sulfur, such that when X represents oxygen, $X^1$ represents sulfur, and when X represents sulfur, $X^1$ represents oxygen; and each of c, d, e, f and g represents an integer of from 1 to 15, such that the sum of $c+d+e+f+g$ represents an integer of from 6 to 19, and such that at least one third of the total of all of the X's plus all the $X^1$'s represents sulfur atoms and at least two consecutive X's and/or $X^1$'s in the structure of the compound are sulfur atoms.

Typical diols include the following:

(1) 3,6-dithia-1,8-octanediol:- $HOCH_2CH_2SCH_2CH_2SCH_2CH_2OH$
(2) 3,6,9-trithia-1,11-undecanediol:- $HOCH_2CH_2SCH_2CH_2SCH_2CH_2SCH_2CH_2OH$
(3) 3,6,9,12-tetrathia-1,14-tetradecanediol:- $HO(CH_2CH_2S)_4CH_2CH_2OH$
(4) 9-oxo-3,6,9,12,15-tetrathia-1,17-heptadecanediol:- $HO(CH_2CH_2S)_2CH_2CH_2O(CH_2CH_2S)_2CH_2CH_2OH$
(5) 9,12-dioxa-3,6,15,18-tetrathia-1,20-eicosanediol:- $HO(CH_2CH_2S)_2(CH_2CH_2O)_2(CH_2CH_2S)_2(CH_2OH)$
(6) 3,6-dioxa-9,12-dithia-1,14-tetradecanediol:- $HO(CH_2CH_2O)_2(CH_2CH_2S)_2CH_2CH_2OH$
(7) 3,12-dioxa-6,9-dithia-1,14-tetradecanediol:- $HOCH_2CH_2O(CH_2CH_2S)_2CH_2CH_2OCH_2CH_2OH$
(8) 3,18-dioxa-6,9,12,15-tetrathia-1,20-eicosanediol:- $HOCH_2CH_2O(CH_2CH_2S)_4CH_2CH_2OCH_2CH_2OH$
(9) 12,18-dioxa-3,6,9,15,21,24,27-heptathia-1,29-nonacosanediol:$HO(CH_2CH_2S)_3CH_2CH_2OCH_2CH_2SCH_2CH_2O(CH_2CH_2S)_3CH_2CH_2OH$
(10) 6,9,15,18-tetrathia-3,12,21-trioxo-1,23-tricosanediol:$HOCH_2CH_2O(CH_2CH_2S)_2CH_2CH_2O(CH_2CH_2S)_2CH_2CH_2OCH_2CH_2OH$.

Water-soluble sulfur-containing dibasic acids which can be used include those having the formula: $HOOCCH_2(SCH_2CH_2)_qSCH_2COOH$, in which q represents an integer of from 1 to 3, and the alkali metal and ammonium salts of said acids. Typical illustrative examples include:

(1) ethylene-bis-thioglycolic acid:- $HOOCCH_2SCH_2CH_2SCH_2COOH$
(2) 3,6,9-trithiahendecane dioic acid:- $HOOCCH_2(SCH_2CH_2)_2SCH_2COOH$
(3) 3,6,9,12-tetrathiatetradecanedioic acid:- $HOOCCH_2(SCH_2CH_2)_3SCH_2COOH$
(4) ethylene-bis-thioglycolic acid disodium salt
(5) ethylene-bis-thioglycolic acid dipotassium salt
(6) ethylene-bis-thioglycolic acid diammonium salt
(7) 3,6,9-trithiahendecane dioic acid disodium salt
(8) 3,6,9,12-tetrathiatetradecanedioic acid disodium salt.

The complexing agent, if included in the emulsion, must not desensitize the emulsion. Various complexing agents which can be incorporated in the emulsion layers of the photographic element without adversely affecting the element include thiouronium and isothiouronium salts, such as 2,2'-methylsulfonylimino bis(ethyl isothiouronium para toluene sulfonate), 3,5-thiouronium-1-methyl-1-propane sulfonate, 3,5-thiouronium-1-propane sulfonate, and the like as described in U.S. Pat. Nos. 3,531,285 and 3,301,678; aminothiazolines such as 2-amino-2-thiazolium trichloroacetate and the like, azo thioethers and blocked azolinethiones such as those described, for example, in U.S. Pat. No. 3,824,103 and complexing agents such as those described in U.S. Pat. No. 3,785,830.

If the complexing agent is incorporated in the activator sheet, any of the above complexing agents can be used in addition to other complexing agents such as thiourea and the like.

The activator sheet can also contain a thermal solvent, if desired, to aid the acid in diffusing to the emulsion layer. The thermal solvent should be added if the depressed melting point of the mixture of the diffusible acid and the complexing agent, if any, is 200° C. or higher. The thermal solvents can, at any rate, accelerate the rate of bleaching by depressing the melting point of the mixture.

By the term "thermal solvent" it is meant a non-hydrolyzable organic material which is a solid at ambient temperatures, but which has a mixed melting point with the other ingredients at or below the temperature of the thermal process employed. Preferred thermal solvents for this invention include a variety of ethers, sugars and alcohols which act as solvents for the incorporated materials functioning in the process.

Examples of useful thermal solvents can be found in U.S. Pat. No. 3,667,959 issued June 6, 1972; U.S. Pat. No. 3,347,675 issued Oct. 17, 1967 and U.S. Pat. No. 3,438,776 issued Apr. 15, 1969 and include non-hydrolyzable polar solvents containing up to 10 carbon atoms such as ethylene glycol, and low molecular weight polyethylene glycol and polyethylene oxide, 1,10-decane diol, 1,6-hexanediol, sorbitol and the like.

In accordance with the invention, a catalyst need not be incorporated in either the photographic emulsion or the acidic processing web at the specified pH of 4.0 or less.

Other addenda such as bleaching compounds, dye bleach competers, and fixing compounds known in the art can be incorporated into the activator sheet of this invention.

In order to satisfactorily bleach out the silver image in the absence of a silver dye-bleach catalyst with a brief heating step, the activator sheet must have a pH not greater than 4.0 and must have a melting point sufficiently low to enable the acid at processing temperatures to diffuse to the emulsion layer, i.e., a melting point below about 200° C., such as within the range of about 50° C. to about 150° C. Thus, the strength and proportion of the acid can be adjusted to achieve the low pH values and the use of the thermal solvent can lower the melting point of acids having higher melting points in order to achieve these properties.

It is pointed out that if gelatin is used as a binder in the emulsion layers, since it is a buffer, more acid should be used. Binders which are not buffers may require the use of less acid.

The acid component as described can be present in a range of concentration in the activator sheet so long as the effective pH of the layer or layers in the sheet is 4.0 or less. Preferably the acid is present from about 1.0 g/m$^2$ to about 50.0 g/m$^2$ in the activator sheet. The polymeric vehicle preferably is present from about 1.0 g/m$^2$ to about 50.0 g/m$^2$ in the activator sheet. Typical concentrations for complexing agents are from about 1.0 g/m$^2$ to about 50.0 g/m$^2$ or (about 1 mole to about 5 mole/mole of silver halide). Thermal solvents can be present from about 1.0 g/m$^2$ to about 50.0 g/m$^2$.

The activator sheet can be prepared by coating onto a suitable support a coating composition comprising the acid, the vehicle, optionally the complexing agent, the thermal solvent and then drying. The various components are coated from a solvent such as methanol, ethanol, acetone, water, or the like. The various components can be coated in one layer or in different adjacent layers.

A typical activator sheet or web comprises the following components

| | |
|---|---|
| thiourea | 5.4 g/m$^2$ |
| 1,6-hexanediol | 5.4 g/m$^2$ |
| p-toluenesulfonic acid | 5.4 g/m$^2$ |
| poly(vinylpyrrolidone) | 2.7 g/m$^2$ |
| Triton TX-100 (Surfactant which is a sodium salt of an alkyl aryl polyether sulfonate) | 1.25 ml (10% solution) | in methanol/distilled water (50:50 parts by volume.

This activator sheet or web has an effective pH of 4.0 or less.

The silver and dye images are bleached by merely placing the activator sheet over the image and laminating by applying heat at the melting point of the components in the activator sheet and lightly pressing the two sheets together, such as with a roller or other suitable means. Excessive pressure in pressing the two sheets together should be avoided.

A positive dye image is produced in the element by bleaching upon briefly heating the laminate, preferably to a temperature of about 50° C. to about 150° C. and more preferably from about 90° C. to about 120° C. over a time period ranging from about 2 to about 300 seconds, preferably from about 15 to 30 seconds. The temperature and length of heating can be varied widely depending on the thickness of the emulsion, activator chemistry layers, desired image, and the like. Excessive pressure on the laminate during the described heating step is to be avoided. Undue pressure on the laminate during this step can provide less than an optimum dye image.

Any suitable means can be useful to provide the desired processing temperature. The heating means can be a simple hot plate, iron, roller, oven or the like.

Processing is usually carried out under atmospheric conditions of pressure and humidity.

In a preferred embodiment, the support for the activator sheet is transparent so that the image is visible through the activator sheet. It is a particular advantage of this invention that the activator sheet need not be delaminated from the image. The resulting photographic element comprises a support having thereon a first layer containing a silver metal image and overall bleachable dye and laminated to the dye image a transparent second layer, in the absence of a silver dye-bleach catalyst, comprising (a) a nonvolatile, diffusible acid selected from the group consisting of nonvolatile, diffusible mineral acids and organic acids containing up to 10 carbon atoms and (b) a non-hydrolyzable polymeric vehicle wherein said second layer or layers has an effective pH of up to 4.0 and is solid up to at least about 50° C. with a melting point lower than 200° C.

Alternatively, the resulting photographic element can comprise a support having thereon a first layer containing a silver metal image and overall bleachable dye and laminated thereon a transparent second layer, in the absence of a silver dye-bleach catalyst, comprising (a) a nonvolatile, diffusible acid selected from the group consisting of nonvolatile, diffusible mineral acids and organic acids containing up to 10 carbon atoms (b) a silver halide complexing agent and (c) a non-hydrolyzable polymeric vehicle wherein said second layer or layers has an effective pH of up to 4.0 and is solid up to at least about 50° C. with a melting point lower than 200° C. As described, each of the photographic elements can contain more than one transparent second layer, if desired. In a preferred embodiment, these layers are contiguous to produce the desired interaction upon processing.

The photographic element can be prepared using any source for the silver image. For example, the silver image can be provided by imagewise exposing a photographic emulsion containing a silver salt such as silver behenate, silver laurate, silver trifluoroacetate and silver halide such as silver chloride, silver chlorobromide, or the like to provide a latent image and chemically developing or physically developing the latent image in a conventional developer bath or by heat if using a photothermographic element.

In yet another embodiment, a silver image with an overall dye covering can be obtained by simply depositing silver through a mask and overall depositing the bleachable dye.

The bleachable dyes used herein are well known in the art. The term "bleachable dyes" as used herein includes compounds which are dye precursors, i.e., colorless compounds which become colored during processing of the photographic materials and shifted dyes which shift hypsochromically or bathochromically to the desired image hues when subjected to a different environment such as a change in pH, reaction with a material to form a complex, etc. The term "non-diffusible" as used herein refers to bleachable dyes which in themselves are non-diffusible in the emulsion, or dyes which are rendered non-diffusible by the use of a suitable mordant, such as those described in U.S. Pat. No. 2,882,156. The elements of this invention can have a single emulsion coating for monochrome dye images formed from either one or a mixture of bleachable dyes, which dye images are either colored or neutral (e.g., black and white) images. Primarily, azo dyes are used in silver dye-bleach systems because the bleaching process cleaves the —N=N— double bond to give two aromatic fragments. Typical azo dyes which can be used in the practice of this invention are listed in numerous patents, some of which are U.K. Pat. Nos. 923,265; 999,996; 1,042,300; 1,077,628; and U.S. Pat. Nos. 3,178,290; 3,178,291; 3,183,225 and 3,211,556.

Bleachable dyes include those known in the art and dyes such as disclosed in the Color Index (third edition) published by the Society of Dyers and Colourists, copyright 1971, printed by Lund Hymphreys, Bradford and London, provided they are bleachable as herein described. This includes bleachable dyes such as azo dyes, formazan dyes, azoxy dyes, xanthene dyes, azine dyes, phenylmethane dyes, nitroso dyes, indigo dyes, quinones, nitro-substituted dyes, phthalocyanines, and others known to one skilled in the art. Precursors to these dyes as known in the art, such as, hydrazo or diazonium compounds to yield azo dyes, tetrazolium salts to yield formazan dyes, etc., are also useful herein.

The bleachable dyes are defined as those dyes which in the presence of a photographic image comprised of silver metal and an aqueous solution of a silver complexing agent such as thiourea, in the absence of a silver dye-bleach catalyst, at pH values up to 4.0 suffer discharge of their color proportionate to the amount of silver metal present. Further examples of these dyes may be found in U.S. Pat. Nos. 3,202,511; 3,493,372 and U.K. Pat. Nos. 1,146,118 and 1,255,857.

The elements of this invention may have a plurality of coatings each containing a different bleachable dye for providing multicolor images. Especially useful arrangements are those in which at least three light-sensitive emulsion layers are provided which are respectively sensitized to blue, green and red radiation, and contain, respectively, non-diffusible yellow, magenta and cyan dyes. The emulsions used in this invention can contain the bleachable dyes. However, it is also possible, and sometimes preferable, to incorporate the bleachable dye in an alkaline-permeable layer contiguous to the emulsion layer. This arrangement provides increased speed, especially when the bleachable dye containing layer is coated adjacent to the emulsion layer. Thus, in one useful arrangement, a support has coated thereon, in the following orders, layers containing, respectively, blue-sensitive silver halide, bleachable yellow dye; green-sensitive silver halide; bleachable magenta dye; red-sensitive silver halide; and bleachable cyan dye.

The dyes can be added by any of the conventional methods known in the art, for example, as dispersions in which ballasted dyes are rendered partially soluble by use of a sulfonic acid or carboxylic acid substituent; or as dispersions wherein an oil soluble dye is dispersed alone or in the presence of a high boiling solvent in the photographic binder.

In the silver dye-bleach system, photographically developed silver is used to reduce a dye from a colored to a colorless form. This dye bleaching step is usually carried out in an acidic solution in the presence of a silver ion complexing agent and a dye bleach catalyst. In this invention, a dry sheet is provided to carry out the bleach step at an effective pH up to 4.0 in the absence of a silver dye-bleach catalyst.

The bleachable dyes are preferably used at a concentration ranging from about 0.1 g/m$^2$ to about 3.00 g/m$^2$ to achieve a discernible image, depending on the molar extinction coefficient of the dye, and whether a reflection print or transparency is desired.

In the preferred embodiment the photographic element is completely dry processed, i.e., in the absence of any processing solutions or baths. The silver image is preferably produced by a photothermographic process using a photothermographic element.

Typical photothermographic elements to which the bleachable dyes are added are described in U.S. Pat. No. 3,785,830 of Sullivan, Cole and Humphlett, U.S. Pat. No. 3,301,678 and U.S. Pat. No. 3,531,285 both by Haist, Humphlett and Johnson and U.S. Pat. No. 3,801,321 of Evans and McLaen.

Other photothermographic elements which are processed by heat include those containing a silver salt and a base precursor such as the salt of trifluoroacetic acid, and an amine, or bis-isothiuronium compound such as those described in U.S. Pat. Nos. 3,669,670; 3,301,678 and 3,531,285.

The photothermographic element can comprise a support having thereon a reducing agent, a silver salt oxidizing agent, and a photosensitive silver halide composition. Typically, preferred photothermographic elements are described in U.S. Pat. Nos. 3,785,830; 3,801,321; 3,301,678 and 3,531,285.

Various reducing agents useful in photothermographic compositions containing bleachable dyes and optionally silver complexing agents are for example, polyhydroxybenzenes such as hydroquinone developing agents including, for instance, hydroquinone, alkyl substituted hydroquinones, exemplified by tertiarybutylhydroquinone, methylhydroquinone, 2,5-dimethylhydroquinone and 2,6-dimethylhydroquinone; catechols and pyrogallol; halo-substituted hydroquinones such as chlorohydroquinone or dichlorohydroquinone; alkoxy substituted hydroquinones such as methoxyhydroquinone or ethoxyhydroquinone and the like. Other reducing agents such as anhydro dihydro piperidino hexose reductone; hydroxytetronic acid reducing agents and hydroxy tetronimide developing agents; 3-pyrazolidinone developing agents such as 1-phenyl-3-pyrazolidinone and 4-methyl-4-hydroxymethyl-1-phenyl-3-pyrazolidinone and those described in British Pat. No. 930,572 published July 3, 1963; certain hydroxylamine developing agents; ascorbic acid developing agents such as ascorbic acid, ascorbic acid ketals, and other ascorbic acid derivatives; phenylenediamine developing agents; certain aminophenol developing agents and the like. Combinations of reducing agents can also be employed. Preferred reducing agents are sulfonamidophenols such as 2,6-dichloro and 2,6-dibromo-4-benzenesulfonamidophenols as described in U.S. Pat. No. 3,801,321 and bis-beta-naphthols such as described in U.S. Pat. No. 3,751,249.

The silver salt oxidizing agent can be a silver salt of a long chain fatty acid such as silver behenate, silver stearate, silver oleate, silver laurate, silver hydroxystearate, silver caprate, silver myristate and silver palmitate as well as silver benzoate, silver phthalate, silver acetate, silver phthalazinone, silver benzotriazole and silver saccharin. A particularly useful silver salt herein is a silver salt of a thione. The silver salt of the thione can be prepared in situ in the photothermographic materials by combining a source of silver, such as silver trifluoroacetate, with the thione compound in the composition. The thione compound is a compound represented by the formula:

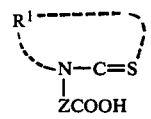
ZCOOH wherein $R^1$ represents atoms completing a 5-member heterocyclic nucleus, such as a thiazoline nucleus, and Z is alkylene, such as alkylene containing 1 to 30 carbon atoms, typically 1 to 10 carbon atoms. Examples of suitable 5-member heterocyclic nuclei are thiazoline-2-thione, benzothiazoline-2-thione, imidazoline-2-thione or similar heterocyclic thione nucleus. The heterocyclic nucleus can contain substituent groups which do not adversely affect the described photothermographic materials such as alkyl containing 1 to 3 carbon atoms, or phenyl. Alkylene as employed herein includes so called branched chain alkylene such as

An especially suitable silver salt forming thione compound is a thiazoline-2-thione represented by the formula:

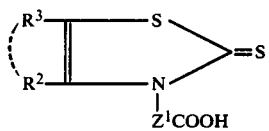

wherein $Z^1$ is alkylene containing 1 to 4 carbon atoms, typically methylene; $R^2$ and $R^3$ are each selected from the group consisting of hydrogen, alkyl containing 1 to 4 carbon atoms, and aryl containing 6 to 10 carbon atoms, or taken together are atoms completing a benzo group. The alkyl, aryl and benzo groups can be substituted with groups which do not adversely affect the described photothermographic materials.

Another suitable silver salt forming thione compound is an imidazoline-2-thione represented by the formula:

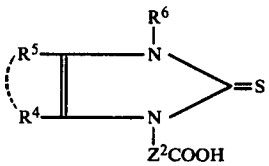

wherein $Z^2$ is alkylene containing 1 to 4 carbon atoms, typically ethylene; $R^6$ is alkyl, typically alkyl containing 1 to 3 carbon atoms, such as methyl, ethyl or propyl, aryl containing 6 to 10 carbon atoms, such as phenyl, or carboxyalkyl, such as carboxyethyl and carboxymethyl; $R^4$ and $R^5$ are each selected from the group consisting of hydrogen, alkyl containing 1 to 4 carbon atoms, such as methyl, ethyl and propyl, aryl containing 6 to 10 carbon atoms, such as phenyl or tolyl, or $R^4$ and $R^5$ taken together are atoms completing a benzo group.

A further suitable silver salt forming thione compound is an oxazoline-2-thione represented by the formula:

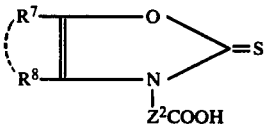

wherein $Z^2$ is as described; $R^7$ and $R^8$ are each selected from the group consisting of hydrogen, alkyl containing 1 to 4 carbon atoms, such as methyl, ethyl, and propyl, aryl containing 6 to 10 carbon atoms, such as phenyl or tolyl, or $R^7$ and $R^8$ taken together are atoms completing a benzo group.

Examples of suitable thione compounds within the described formulas include:

3-(2-carboxyethyl)-4-methyl-4-thiazoline-2-thione,
3-(2-carboxyethyl)benzothiazoline-2-thione,
3-(2-carboxyethyl)-5-phenyl-1,3,4-oxadiazoline-2-thione,
3-(2-carboxyethyl)-5-phenyl-1,3,4-thiadiazoline-2-thione,
3-(carboxymethyl)-4-methyl-4-thiazoline-2-thione,
3-(2-carboxyethyl)-1-phenyl-1,3,4-triazoline-2-thione,
1,3-bis(2-carboxyethyl)imidazoline-2-thione, 1,3-bis(2-carboxyethyl)benzimidazoline-2-thione,
3-(2-carboxyethyl)-1-methylimidazoline-2-thione,
3-(2-carboxyethyl)benzoxazoline-2-thione, and
3-(1-carboxyethyl)-4-methyl-4-thiazoline-2-thione.

The described thione compounds can be prepared employing processes known in the art. The described silver complexes of the thione compounds can be prepared in situ, as described, or the silver complexes can be isolated.

The photosensitive silver halide useful herein can include, for example, silver chloride, silver bromide, silver bromoiodide, silver chlorobromoiodide, or mixtures thereof. For the purposes of the invention, silver iodide is also included as a photosensitive silver halide. While the photosensitive silver halide can be prepared in situ in the photothermographic material, this is not necessary according to the invention. The photosensitive silver halide can be coarse or fine-grain, very fine-grain photosensitive silver halide being especially useful. The photosensitive silver halide can be prepared by any of the well-known procedures employed in the photographic art. The silver halide can be prepared, for example, employing single-jet preparation techniques, double-jet preparation techniques, such as techniques employed in preparing Lippman emulsions and the like. Surface image or internal image silver halide materials can be used. If desired, mixtures of surface and internal image silver halide materials can be used. Negative type silver halide is typically employed. The silver halide materials can be regular grain such as described in Klein and Moisar, *Journal of Photographic Science*, Volume 12, No. 5, September-October (1964), pages 242–251.

The photosensitive silver halide can be chemically sensitized employing techniques known in the photographic art. Although a binder is not essential with the photothermographic materials described, a binder is typically employed. The binders which are useful with the described photothermographic materials include various colloids employed alone or in combination as vehicles and/or binding agents which do not adversely affect the desired photothermographic properties of the described compositions and in various layers of a photothermographic element. Suitable materials can be hydrophilic or hydrophobic. The binders which are suitable are transparent or translucent and include both naturally-occurring substances such as proteins, for example, gelatin, gelatin derivatives, cellulose derivatives, polysaccharides such as dextran, gum arabic and the like; and synthetic polymeric substances such as water soluble polyvinyl compounds like poly(vinylpyrrolidone), acrylamide polymers and the like. Other synthetic polymeric compounds which can be employed include dispersed vinyl compounds such as in latex form and particularly those which increase dimensional stability of photothermographic materials. Suitable binders include polymers such as water insoluble polymers of alkyl acrylates or methacrylates and those which have cross-linking sites which facilitate hardening or curing as well as those having recurring sulfobetaine units. Especially suitable binding agents include high molecular weight materials and resins such as poly(vinyl butyral), cellulose acetate butyrate, poly(methyl methacrylate), poly(vinylpyrrolidone), ethyl cellulose, poly(styrene), poly(vinyl chloride), chlorinated rubber, poly(isobutylene), butadienestyrene copolymers, vinyl chloride-vinyl acetate copolymers, copolymers of vinyl acetate, vinyl chloride and maleic acid, poly(vinyl alcohol), high molecular weight ethylene oxide polymers and active methylene polymers such as those described in U.S. Pat. No. 3,904,418 by Ponticello and Mowrey.

The photothermographic composition can be coated on a wide variety of supports. Useful supports include those which can withstand the processing temperatures employed such as cellulose ester film, poly(vinyl acetal) film, polystyrene film, poly(ethylene terephthalate) film, polycarbonate film and related films or resinous materials, as well as glass, paper, metal and the like. Typically a flexible support is employed.

Hardenable layers of a photothermographic element, as described, can be hardened by various organic or inorganic hardeners alone or in combination, such as aldehydes, ketones, vinyl sulfones, aziridines, mucrochloric acid and the like which do not adversely affect the sensitometric properties of the photothermographic materials. Hardeners which cause adverse reduction of the described composition should be avoided.

The photothermographic elements and materials according to the invention can contain addenda and layers commonly employed in photothermographic elements, such as antistatic and/or conducting layers, plasticizers and/or lubricants, surfactants, matting agents, brightening agents, light-absorbing materials, filter dyes, antihalation dyes and absorbing dyes, and the like.

The various components of the photothermographic materials of the invention can be added from water solutions, or suitable organic solvent solutions can be used. The components can be added using various procedures known in the photographic art.

If desired, an agent, sometimes referred to as a toning agent or activator-toning agent, can be employed with the photothermographic materials according to the invention to provide an increase in density at certain processing temperatures. Suitable toning agents, also known as activator-toning agents, include cyclic imide toning agents such as phthalimide, N-hydroxyphthalimide, succinimide, and N-hydroxysuccinimide, and the like. These are described, for instance, in Belgian Pat. No. 766,590, issued June 15, 1971. Sulfolane in some instances can provide improved results in the described photothermographic compositions. Some photothermographic elements and compositions described according to the invention do not need a toning agent.

Spectral sensitizing dyes can be used conveniently to confer additional sensitivity to the light sensitive silver halide employed according to the invention. For instance, additional spectral sensitization can be obtained by treating the silver halide with a solution of a sensitizing dye in an organic solvent or the dye can be added in the form of a dispersion. Spectral sensitizers which can be used include the cyanines, merocyanines, complex-(trinuclear or tetranuclear) merocyanines, complex (trinuclear or tetranuclear) cyanines, holopolar cyanines, styryls, hemicyanines, such as enamines, oxonols, and hemioxonols.

A range of concentrations of each component in the photothermographic material can be employed. Typically, each light sensitive layer of a photothermographic element according to the invention can comprise (a) from about 0 to about $1.0 \times 10^{-1}$ moles of silver as the described complex and (b) about $1.0 \times 10^{-3}$ to about $1.0 \times 10^{-2}$ moles of the described photosensitive AgX per square meter of support and (c) a reducing agent in at least molar equivalency to conduct development based on reducible silver ions and up to 10 times equivalent in excess. An optimum concentration of each component will depend upon the particular components, the desired image, processing temperature and the like.

The bleachable dye can be added directly to the photothermographic composition prior to coating or can be added after the composition is applied to the support.

The photothermographic layer and/or other layers of a photothermographic element according to the invention can be coated by various coating procedures including dip coating, airknife coating, curtain coating or extrusion coating using hoppers of the type described in U.S. Pat. No. 2,681,294 of Beguin, issued June 15, 1954. If desired, two or more layers can be coated simultaneously by procedures known in the art.

The silver image on the photothermographic element can be produced after imagewise exposure within a short time by merely moderately overall heating the photothermographic element. For instance, a visible image on a photothermographic element according to the invention can typically be produced within a few seconds, e.g. about 1 to about 60 seconds after exposure by heating the element to a temperature within the range of about 100° C. to about 250° C., typically a temperature within the range of about 130° C. to about 180° C. Usually, the time of heating is less than about 20 seconds, such as about 2 to 5 seconds at a temperature of about 180° C. Optimum time of heating and optimum temperature of heating can be determined employing test procedures well known in the art.

One embodiment of the invention accordingly is a method of developing and stabilizing an image in an exposed photothermographic element comprising a support having thereon (a) a reducing agent, as described, (b) a silver salt of a thione compound, also as described, (c) a photosensitive component consisting essentially of photosensitive silver halide, (d) a bleachable dye and, if desired (e) a binder, comprising heating the photothermographic element to a temperature within the range of about 100° C. to about 250° C.

In developing an image in a photothermographic element according to the invention, increasing or decreasing the length of time of heating can enable use of a higher or lower temperature within the described range.

In some cases it may be convenient to produce the positive dye image using only a single heating step. This can be accomplished by placing a timing layer between the photothermographic element and the activating sheet and exposing and heat processing whereby the bleaching is delayed until the silver image is developed.

If moisture is present in the activator sheet, the sheet should be preheated to a molten state prior to laminating to release excess moisture and prevent gas bubbles when the dry activator sheet is laminated to the silver dye image.

The invention is further illustrated by the following examples.

EXAMPLE 1

A heat-developable photographic element was prepared by combining the following components and coating on a suitable paper support:
A. A sulfur and gold sensitized, cubic-grained silver bromide emulsion (0.4 gAg/m²)
B. 1-Phenyl-3-pyrazolidone (1.08 g/m²)
C. 1,8-(3,6-Dioxoactane)-bis-isothiuronium-p-toluenesulfonate (3.24 g/m²)
D. α,α-bis[4-3',6'-disulfo-8'-heptoylamino-1'-naphthol-2'-yl)azo-2,5'-dimethylphenyl]toluene, tetrasodium salt (0.2 g/m²)
E. Gelatin (6.75 g/m²).

A sample of the above prepared element was imagewise exposed to tungsten light through a graduated-density test object to provide a latent image which was then thermally developed by contacting the sample for 5 seconds with a heated metal block having a temperature of 200° C. A negative silver scale was produced. Two samples were then laminated in contact, in the absence of a silver dye-bleach catalyst, with the following activator sheet, at an effective pH of less than 4.0, for 15 seconds at 100° C. both freshly coated and after one hour. The activator sheet comprised a film support having coated thereon Sulfonated polystyrene: 1.8 g/m²
Thiourea: 10.8 g/m²
p-Toluenesulfonic acid: 10.8 g/m²
1,10-Decanediol: 10.8 g/m²

Positive magenta dye images were observed which gave excellent uniform bleaching and good minimum densities. The equivalent results indicated fresh activity of the activator sheet and activity after one hour were equal.

In a similar manner, 1,6-hexanediol and ethyleneglycol were used as replacements for 1,10-decanediol and similar results were obtained.

Effective silver halide solvents which replaced thiourea were also shown, including:

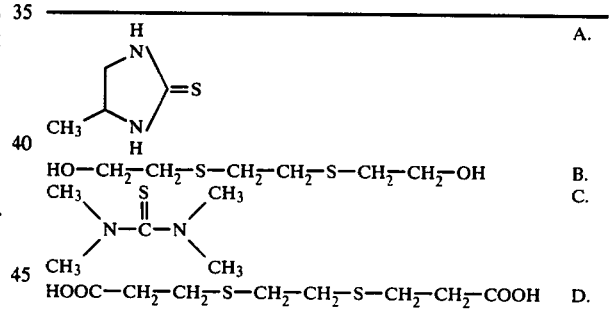

EXAMPLE 2

Comparative Example

A photographic element containing a cellulose acetate support having coated thereon 2.90 g of AgBr/m² and the azo dye having the structure

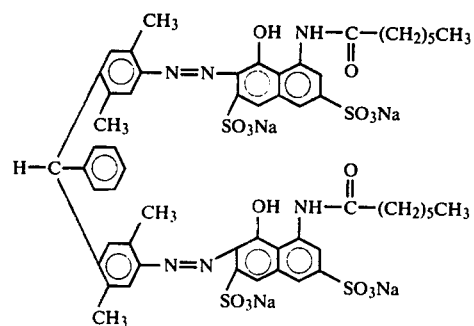

was imagewise exposed and processed for 3 minutes in Kodak Developer D19, fixed and dried. The dried negative silver image was bleached by laminating it to an activator web coated on a polyethylene terephthalate support, in the absence of a silver dye-bleach catalyst, at an effective pH of less than 4.0, for 20 seconds at 90° C. The preparation contained the following compounds coated thereon (per square meter):

| | | |
|---|---|---|
| Thiourea | 5.4 | g |
| Distilled water | 54 | ml |
| Sulfonated polystyrene (18.3% solution in water) | 10.8 | ml |
| Polyacrylic acid (Acrysol (A-3) (25% solution) | 10.8 | ml |
| Hydrochloric acid | 10.8 | ml |
| Distilled water containing 6% saponin | 5.4 | ml |

A positive dye image was formed. However, the activator web was unsatisfactory because the hydrochloric acid was found to be too volatile.

EXAMPLE 3

A sample of photothermographic element was prepared by combining the following components and coating on a suitable paper support:
A. A sulfur and gold sensitized cubic grained silver bromide emulsion (0.43 gAg/m$^2$).
B. 1-phenyl-3-pyrazolidone (1.08 g/m$^2$).
C. Dimethyldodecylammonium hydrogen malonate (3.24 g/m$^2$).
D. α,α-bis[4-3',6'-disulfo-8'-heptoylamino-1'-naphthol-2'-yl) azo-2,5'-dimethylphenyl]toluene, tetrasodium salt (0.21 g/m$^2$).
E. Gelatin (6.75 g/m$^2$).
F. 2,2'-methyl sulfonyl imino bis(ethyl isothiouronium para-toluene sulfonate) (3.24 g/m$^2$).

A sample was exposed with tungsten light through a graduated density test object to provide a latent image which was thermally developed as in Example 1 for 30 seconds at 150° C. The element was then laminated, in the absence of a silver dye-bleach catalyst, with an activator sheet comprising a polyester film support having coated thereon, at an effective pH of less than 4.0, a layer containing polyacrylic acid at 2.7 g/m$^2$ and p-toluenesulfonic acid at 5.4 g/m$^2$. The complexing agent was the isothiouronium salt in the emulsion layer. The laminated structure was then heated to 100° C. and after one minute a well-defined positive magenta dye image was obtained.

EXAMPLE 4

A photothermographic element, as described in Example 3 with the exception that the support was a poly(ethylene terephthalate) film support, was exposed through a graduated-density test object and directly laminated with an acid activator sheet comprising a polyester film support comprising (a) a first layer containing titanium dioxide at 21.6 g/m$^2$ and gelatin at 2.16 g/m$^2$ and overcoated with (b) a second layer containing polyacrylic acid at 2.7 g/m$^2$, p-toluene sulfonic acid at 5.4 g/m$^2$ and thiourea at 5.4 g/m$^2$. The laminated structure was then thermally processed by contact for one minute with a metal block heated to 150° C. A reflection print comprising a well-defined, positive magenta dye image resulted which indicated that silver development and bleaching were carried out in a single heating step, presumably due to the voluminous TiO$_2$ layer acting as a timing layer for the silver-dye bleach reaction.

EXAMPLE 5

This example illustrates the use of a photothermographic material, such as described in Evans and McLaen U.S. Pat. No. 3,801,321, to produce a dye image according to the practice of this invention:

A silver behenate/behenic acid dispersion was prepared by ball-milling the following components for 72 hours:
Silver behenate: 33.6 g
Behenic acid: 25.4 g
Poly(vinyl butyral): 12.0 g
Acetone/toluene (1:1 by volume): 675 ml Photothermographic elements were then prepared by combining the following addenda and coating the composition at 0.006 inch on a polyethylene terephthalate film support both with and without a titanium dioxide reflective layer:

| | | |
|---|---|---|
| Silver behenate dispersion (as prepared above) | 2.0 | ml |
| Silver bromoiodide emulsion peptized in poly(vinyl butyral) (3.0 1/mole Ag, 100 g polymer/mole Ag, 6 mole % iodine) | 2.0 | ml |
| Poly(vinyl butyral) (2½ wt. % of an acetone/toluene solution) | 2.0 | ml |
| Azo dye having the structure | 40 | mg |

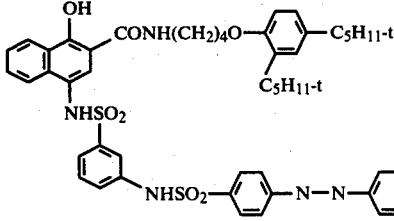

| | | |
|---|---|---|
| 2,6-Dichloro-4-benzenesulfonamido-phenol | 60 | mg |
| 1,8-(3,6-Dioxaoctane)bis-iso-thiuronium-p-toluene sulfonate | 100 | mg |

Samples of the coatings were exposed through a graduated-density test object and thermally developed for 30 seconds at 150° C. The developed samples, which contained a negative silver image and a uniform distribution of dye, were then laminated with an acid activator sheet prepared by coating the following composition on a polyethylene terephthalate film support at a wet thickness of 0.006 inch:

Polyacrylic acid (Acrysol A-3) (25 wt. % aqueous solution): 10 ml
Thiourea: 5 g
p-Toluene sulfonic acid: 5 g
Ethanol/water (1:1 by volume to total volume of 81 ml The laminated structures were heated to 120° C. for 30 seconds and well-defined, positive dye images were obtained.

EXAMPLE 6

A photothermographic material was prepared by the following steps:

(1) A silver thiazoline thione complex was prepared by combining the following addenda and blending for 45 minutes at 48.9° C.

3-(2-carboxyethyl)benzothiazoline-2-thione: 14.8 g
Silver trifluoroacetate: 5.25 g
Isopropyl alcohol: 27 ml
Distilled water (2) A developer toner solution was prepared as follows:

Methanol: 30 ml
t-Butylhydroquinone: 3 g
3-Mercapto-1-H-1,2-4-triazole: 20 ml
Methanol to a total volume: 35 ml (3) A final coating composition was prepared by combining the above-identified mixtures in the following proportions:

Silver complex dispersion (as described under (1) above): 105 ml
Developer-toner mixture: 35 ml
Solution containing 10% by weight saponin: 1 ml
Gelatin peptized silver iodide emulsion: 6 ml
Azo dye: 380 ml The final composition was coated at 0.94 milliliters per square decimeter on a polyethylene coated paper support. The photothermographic material was exposed image-wise for 4 seconds and then thermally developed by contact for 15 seconds with a metal block heated to 140° C. A negative silver image and a uniform distribution of magenta dye was observed. The sample was then laminated in contact with a sample of an activator sheet, in the absence of a silver dye-bleach catalyst, at a pH of less than 4.0, and heated to 70° C. for 60 seconds. The activator sheet consisted of a polyethylene terephthalate film support having coated thereon a layer, in the absence of a silver dye-bleach catalyst, comprising 10.8 grams per square meter thiourea, 5.4 grams per square meter ethylene glycol, 1.9 grams per square meter sulfonated polystyrene, and 0.001 liter per square meter sulfuric acid. This layer had a pH of less than 4.0.

After heating, the elements were left laminated and a well-defined positive magenta dye image was observed.

EXAMPLE 7

Use of Multilayer Photographic Silver Halide Element

A dry, activator sheet was prepared by coating the following components in a layer on a paper support:

Poly(vinylpyrrolidone) (binder): 2.69 g/m$^2$
Thiourea (complexing agent): 5.38 g/m$^2$
p-Toluenesulfonic acid (non-volatile, diffusible acid): 5.38 g/m$^2$
1,6-hexanediol (thermal solvent): 8.07 g/m$^2$ A multilayer photographic element was prepared by coating the following layers, respectively, on a poly(ethylene terephthalate) film support:

1. A cyan layer comprising a red-sensitive, sulfur sensitized gelatin peptized silver bromoiodide emulsion (0.2 μm, 2.5 mole % I, 0.38 g/m$^2$), a silver salt of 1H-1,2,4-triazole (1:1 ratio, 0.27 g/m$^2$), azo Dye I (0:26 g/m$^2$), hydroquinone (0.98 g/m$^2$), dihydroxyphenyl acetic acid (0.25 g/m$^2$), and gelatin (4.24 g/m$^2$).

2. A magenta layer comprising a green-sensitive, sulfur sensitized, gelatin peptized silver bromoiodide emulsion (0.2 μm, 2.5 mole % I, 0.38 g/m$^2$) a silver salt of 1H-1,2,4-triazole (1:1 ratio, 0.27 g/m$^2$), azo Dye II (0.19 g/m$^2$), hydroquinone (0.98 g/m$^2$), dihydroxyphenyl acetic acid (0.25 g/m$^2$) and gelatin (4.24 g/m$^2$).

3. A yellow layer comprising a blue-sensitive, sulfur sensitized, gelatin peptized silver bromoiodide emulsion (0.2 μm, 2.5 mole % I, 0.48 g/m$^2$), a silver salt of 1H-1,2,4-triazole (1:1 ratio, 0.38 g/m$^2$), azo Dye III (0.36 g/m$^2$), hydroquinone (0.98 g/m$^2$), dihydroxyphenyl acetic acid (0.25 g/m$^2$) and gelatin (4.95 g/m$^2$).

The azoaniline dyes used in the described layers were as follows:

Dye I
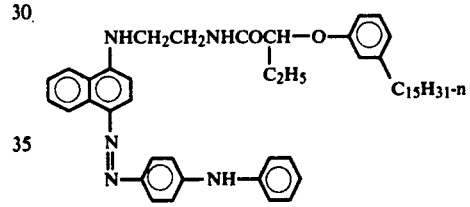

Dye II
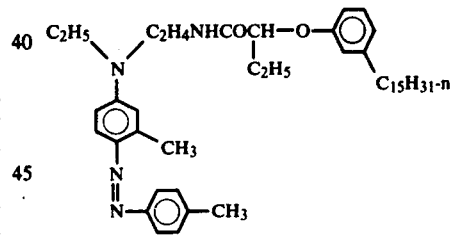

Dye III
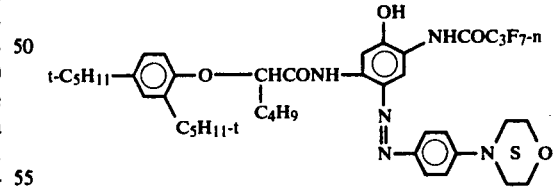

The described photographic element was imagewise exposed for 0.1 second to tungsten light (6100° K) to produce a developable latent image in the element. The photographic element was then uniformly heated at 155° C. for 25 seconds. The resulting element was then laminated to the described dry, activator sheet with the layer containing the p-toluenesulfonic acid in contact with the described top photographic layer of the photographic element. The resulting laminate was heated uniformly for 30 seconds at 120° C. The activator sheet was permitted to remain laminated to the photographic element after this heating step.

A reversal multicolor reflection print with good color separation was produced.

If desired, the described activator sheet after heating as described could be delaminated to produce a reversal color transparency with good color separation.

EXAMPLE 8

A multicolor photothermographic element was prepared by coating a poly(ethylene terephthalate) film support with the layers identified below. The values are stated in mg/ft² with those values in parenthesis denoting conversion to grams/m².

| Layer | AgX[1] | Gel | Dye | Aminimide[5] | Developer[6] |
|---|---|---|---|---|---|
| 1 (overcoat) | — | 200 (2.2) | — | 100 (1.1) | 80 (0.86) |
| 2 (blue-sens.) | 100 Ag (1.1) | 400 (4.3) | 20 (0.22)[2] | 200 (2.2) | 60 (0.65) |
| 3 (interlayer) | — | 200 (2.2) | — | 100 (1.1) | 80 (0.86) |
| 4 (green-sens.) | 80 Ag (0.86) | 400 (4.3) | 20 (0.22)[3] | 150 (1.6) | 50 (0.54) |
| 5 (interlayer) | — | 200 (2.2) | — | 100 (1.1) | 80 (0.86) |
| 6 (red-sens.) | 80 Ag (0.86) | 400 (4.3) | 20 (0.22)[4] | 150 (1.6) | 50 (0.54) |

1. The emulsions employed were sulfur-sensitized, silver bromoiodide emulsions sensitized to the appropriate light source, i.e. blue, green, and red, respectively, with conventional sensitizing dyes. The red and green-sensitive grains were about 0.2μ whereas the blue-sensitive grains were about 0.4μ in size.

2. Bleachable yellow dye:

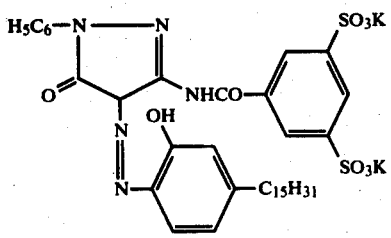

3. Bleachable magenta dye precursor:

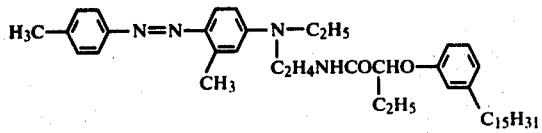

4. Bleachable cyan dye precursor:

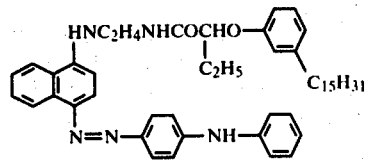

5. Aminimide Base-Release Agent:

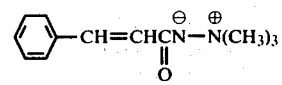

6. The incorporated developing agent is 1-phenyl-3-pyrazolidone.

In addition to the components identified above, all layers contained bis-vinylsulfonylmethyl ether as a hardening agent coated at 5 weight percent based on gelatin and sodium sulfite was present at 20 mg/ft² in Layers 2, 4 and 6.

Process

A sample of the above-prepared element was exposed through a multicolor, graduated-density test object and thermally developed for 20 seconds by contact with a curved metal block heated to 150° C. The developed element, which contained metallic silver images and a uniform distribution of dye in its respectively exposed layers, was then laminated with a silver-dye-bleach activator sheet consisting of a reflective paper support having coated thereon a layer comprising:

Thiourea: 1850 mg/ft² (20 g/m²)
Poly(vinyl pyrrolidone): 462 mg/ft² (5 g/m²)
p-Toluenesulfonic acid: 1850 mg/ft² (20 g/m²)
1,6-Hexanediol: 926 mg/ft² (10 g/m²)

The laminate was thermally treated for 3 minutes by contact with a curved metal block heated to 100° C. The elements remained laminated and well-defined, positive multicolor images having reflective maximum densities greater than 1.5 and minimum densities of less than 0.4 were viewed through the transparent support of the photosensitive element.

The invention has been described in detail with particular reference to preferred embodiments thereof, but it will be understood that variations and modifications can be effected within the spirit and scope of the invention.

What is claimed is:

1. A silver dye-bleach process of thermally dye bleaching a photographic element comprising a silver image in reactive association with a dye that is capable of being bleached in a silver dye-bleach process comprising contacting said image with a dry, activator sheet comprising, in the absence of a silver dye-bleach catalyst, a support having thereon a layer or layers comprising
   (a) a nonvolatile, diffusible acid selected from the group consisting of nonvolatile, diffusible mineral acids and organic acids containing up to 10 carbon atoms;
   (b) a silver halide complexing agent; and
   (c) a non-hydrolyzable polymeric vehicle wherein said layer or layers have an effective pH of up to 4.0 and are solid up to at least about 50° C. with a melting point lower than 200° C. and heating to a temperature from about 50° C. to about 150° C. to laminate the sheet to the element and produce a dye image.

2. The process of claim 1 wherein the activator sheet also contains a non-hydrolyzable thermal solvent containing up to 10 carbon atoms.

3. The process of claim 1 wherein the bleachable dye is an azo dye.

4. The process of claim 1 wherein the non-hydrolyzable polymeric vehicle is selected from the group consisting of poly(styrene sulfonic acid), poly(acrylamide), poly(acrylic acid), poly(vinyl alcohol), poly(ethylene oxide), and poly(vinylpyrrolidone).

5. The process of claim 1 wherein the silver halide complexing agent is thiourea.

6. The process of claim 1 wherein the non-volatile, diffusible mineral or organic acid is selected from the group consisting of phenylphosphoric acid, phenylphosphonic acid, phenylphosphinic acid, sulfuric acid, acetic acid, citric acid, para-toluenesulfonic acid, benzenesulfonic acid, and carboxylic acids containing up to 10 carbon atoms.

7. The process of claim 1 wherein the activator sheet also comprises a thermal solvent that is selected from the group consisting of polyethylene glycol, poly(ethylene oxide), decanediol and hexanediol.

8. The process of claim 1 wherein the activator sheet comprises from about 1.0 g/m$^2$ to about 50 g/m$^2$ of a mineral or organic acid, from about 1.0 g/m$^2$ to about 50 g/m$^2$ of a silver halide complexing agent, and from about 1.0 g/m$^2$ to about 50 g/m$^2$ of a non-hydrolyzable polymeric vehicle.

9. A silver dye-bleach process of thermally dye bleaching a photographic element comprising a silver image in reactive association with a dye that is capable of being bleached in a silver dye-bleach process and a silver halide complexing agent comprising contacting said image with a dry, activator sheet, said activator sheet comprising, in the absence of a silver dye-bleach catalyst, a support having coated thereon a layer or layers comprising
    (a) a nonvolatile, diffusible acid selected from the group consisting of nonvolatile, diffusible mineral acids and organic acids containing up to 10 carbon atoms; and
    (b) a non-hydrolyzable polymeric vehicle
wherein said layer or layers have an effective pH up to about 4.0 and are solid up to at least about 50° C. with a melting point lower than 200° C.; and heating to a temperature from about 50° C. to about 150° C. to laminate the sheet to the element and produce a dye image.

10. The process of claim 9 wherein the silver halide complexing agent is an isothiuronium salt.

11. A silver dye-bleach process of thermally dye bleaching a photographic element comprising a silver image in reactive association with a dye that is capable of being bleached in a silver dye-bleach process comprising contacting said image with a dry, activator sheet comprising, in the absence of a silver dye-bleach catalyst, a support having thereon a layer or layers comprising
    (a) a nonvolatile, diffusible acid selected from the group of nonvolatile, diffusible acids consisting of sulfuric acid, acetic acid, citric acid, para-toluenesulfonic acid, benzenesulfonic acid, phenylphosphonic acid, phenylphosphoric acid, phenylphosphinic acid and carboxylic acids containing up to 10 carbon atoms,
    (b) a silver halide complexing agent, and
    (c) a non-hydrolyzable polymeric vehicle selected from the group consisting of poly(styrene sulfonic acid), poly(ethylene oxide), poly(acrylamide), poly(acrylic acid), poly(vinylpyrrolidone) and poly(vinyl alcohol) non-hydrolyzable polymeric vehicles,
wherein said layer or layers have an effective pH of up to 4.0 and are solid up to at least about 50° C. with a melting point lower than 200° C. and heating to a temperature from about 50° C. to about 150° C. to laminate the sheet to the element and produce a dye image.

12. A silver dye-bleach process of thermally dye bleaching a photographic element comprising a silver image in reactive association with a dye that is capable of being bleached in a silver dye-bleach process and a silver halide complexing agent comprising contacting said image with a dry, activator sheet, said activator sheet comprising, in the absence of a silver dye-bleach catalyst, a support having coated thereon a layer or layers comprising
    (a) a nonvolatile, diffusible acid selected from the group consisting of nonvolatile, diffusible acids consisting of sulfuric acid, acetic acid, citric acid, para-toluenesulfonic acid, phenylphosphonic acid, phenylphosphoric acid, phenylphosphinic acid and carboxylic acids containing up to 10 carbon atoms, and
    (b) a non-hydrolyzable polymeric vehicle selected from the group consisting of poly(styrene sulfonic acid), poly(ethylene oxide), poly(acrylamide), poly(acrylic acid), poly(vinylpyrrolidone) and poly(vinyl alcohol) non-hydrolyzable polymeric vehicles,
wherein said layer or layers have an effective pH up to about 4.0 and are solid up to at least about 50° C. with a melting point lower than 200° C. and heating to a temperature from about 50° C. to about 150° C. to laminate the sheet to the element and produce a dye image.

13. A photographic element comprising a support having thereon a first layer containing a silver metal image in reactive association with a dye that is capable of being bleached in a silver dye-bleach process and laminated to said first layer a transparent second layer, in the absence of a silver dye-bleach catalyst, comprising:
    (a) a nonvolatile, diffusible acid selected from the group consisting of mineral acids and organic acids containing up to 10 carbon atoms;
    (b) a silver halide complexing agent; and
    (c) a non-hydrolyzable polymeric vehicle
wherein said second layer has an effective pH up to 4.0 and is solid up to at least about 50° C. with a melting point lower than 200° C.

14. The photographic element of claim 13 wherein the second layer also comprises a non-hydrolyzable thermal solvent.

15. The photographic element of claim 13 wherein the non-hydrolyzable polymeric vehicle is a member selected from a group consisting of poly(styrene sulfonic acid), poly(acrylamide), poly(acrylic acid), poly(ethylene oxide), poly(vinyl alcohol), and poly(vinylpyrrolidone).

16. The photographic element of claim 13 wherein the silver halide complexing agent is thiourea.

17. The photographic element of claim 13 wherein the mineral or organic acid is selected from the group consisting of phenylphosphoric acid, phenylphosphonic acid, phenylphosphinic acid, sulfuric acid, acetic acid, paratoluenesulfonic acid, benzenesulfonic acid, and carboxylic acids containing 10 carbon atoms or less.

18. The photographic element of claim 13 also comprising a non-hydrolyzable thermal solvent which is selected from the group consisting of polyethylene glycol, poly(ethylene oxide), decanediol, and hexanediol.

19. The photographic element of claim 13 wherein said second layer comprises from about 1.0 g/m$^2$ to about 50 g/m$^2$ of a mineral or organic acid, from about 1.0 g/m² to about 50 g/m² of silver halide complexing agent, and from about 1.0 g/m² to about 50 g/m² of a non-hydrolyzable polymeric vehicle.

20. A photographic element comprising a support having thereon a first layer containing a silver metal image in reactive association with a dye that is capable of being bleached in a silver dye-bleach process and laminated to said first layer a second layer, in the absence of a silver dye-bleach catalyst, comprising
   (a) para-toluenesulfonic acid,
   (b) a poly(vinylpyrrolidone) vehicle,
   (c) a thiourea silver halide complexing agent, and
   (d) a thermal solvent,
wherein said second layer has an effective pH of up to 4.0 and is solid up to at least about 50° C. with a melting point lower than 200° C.

21. A photographic element comprising a support having thereon a first layer containing (i) a silver metal image, (ii) a dye that is capable of being bleached in a silver dye-bleach process, and (iii) silver halide complexing agent and laminated to said first layer a transparent second layer, in the absence of a silver dye-bleach catalyst, comprising
   (a) a nonvolatile, diffusible acid selected from the group consisting of nonvolatile, diffusible mineral acids and organic acids containing up to 10 carbon atoms; and
   (b) a non-hydrolyzable polymeric vehicle
wherein said second layer has an effective pH of up to 4.0 and is solid up to at least about 50° C. with a melting point lower than 200° C.

22. A photographic element of claim 21 wherein the second layer also comprises a non-hydrolyzable thermal solvent.

23. The photographic element of claim 21 wherein the silver halide complexing agent of the first layer is an isothiouronium salt.

24. A photothermographic element comprising a support having thereon, in reactive association, in a binder, a reducing agent, an organic silver salt oxidizing agent, photosensitive silver halide and a dye that is capable of being bleached in a silver dye-bleach process, having thereon an activator sheet, in the absence of a silver dye-bleach catalyst, comprising a support having thereon a layer or layers comprising
   (a) a nonvolatile, diffusible acid selected from the group consisting of mineral acids and organic acids containing up to 10 carbon atoms; and
   (b) a non-hydrolyzable polymeric vehicle
wherein said layer or layers have an effective pH of up to 4.0 and is solid up to at least about 50° C. with a melting point of lower than 200° C.

25. A photothermographic element comprising a support having thereon a first layer comprising a sulfonamidophenol reducing agent, a silver behenate oxidizing agent, photosensitive silver halide, a polymeric binder and a bleachable azo dye, having thereon an activator sheet, in the absence of a silver dye-bleach catalyst, comprising a support having thereon a second layer comprising
   (a) para-toluenesulfonic acid,
   (b) a poly(vinylpyrrolidone) vehicle,
   (c) a thiourea silver halide complexing agent, and
   (d) a thermal solvent,
wherein said second layer has an effective pH of up to 4.0 and is solid up to at least about 50° C. with a melting point lower than 200° C.

26. A silver dye-bleach process of thermally dye bleaching a photothermographic element comprising a silver image in reactive association with bleachable azo dye comprising contacting said image with a dry, activator sheet comprising, in the absence of a silver dye-bleach catalyst, a support having thereon a layer (A) comprising
   (a) para-toluenesulfonic acid,
   (b) a poly(vinylpyrrolidone) vehicle,
   (c) a thiourea silver halide complexing agent, and
   (d) a thermal solvent,
wherein said layer (A) has an effective pH of up to 4.0 and is solid up to at least about 50° C. with a melting point lower than 200° C. and heating to a temperature from about 50° C. to about 150° C. to laminate the sheet to the photothermographic element and produce a dye image.

27. A photothermographic element comprising a support having thereon, in reactive association, in a binder, a reducing agent, an organic silver salt oxidizing agent, photosensitive silver halide and a dye that is capable of being bleached in a silver dye-bleach process, having thereon an activator sheet, in the absence of a silver dye-bleach catalyst, comprising a support having thereon a layer or layers comprising
   (a) a nonvolatile, diffusible acid selected from the group of nonvolatile, diffusible acids consisting of sulfuric acid, acetic acid, citric acid, para-toluenesulfonic acid, benzenesulfonic acid, phenylphosphonic acid, phenylphosphoric acid, phenylphosphinic acid and carboxylic acids containing up to 10 carbon atoms, and
   (b) a non-hydrolyzable polymeric vehicle selected from the group consisting of poly(styrene sulfonic acid), poly(ethylene oxide), poly(acrylamide), poly(acrylic acid), poly(vinylpyrrolidone) and poly(vinyl alcohol) non-hydrolyzable polymeric vehicles,
wherein said layer or layers have an effective pH of up to 4.0 and are solid up to at least about 50° C. with a melting point of lower than 200° C.

28. A photothermographic element comprising a support having thereon a first layer comprising a silver halide developing agent, photosensitive silver halide, a polymeric binder, a thermosensitive base-release agent and a dye that is capable of being bleached in a silver dye-bleach process, having thereon an activator sheet, in the absence of a silver dye-bleach catalyst, comprising a support having thereon a layer (A) comprising
   (a) para-toluenesulfonic acid,
   (b) a poly(vinylpyrrolidone) vehicle,
   (c) a thiourea silver halide complexing agent, and
   (d) a thermal solvent,
wherein said layer (A) has an effective pH of up to 4.0 and is solid up to at least about 50° C. with a melting point lower than 200° C.

* * * * *

UNITED STATES PATENT AND TRADEMARK OFFICE
CERTIFICATE OF CORRECTION

PATENT NO. : 4,168,170
DATED : September 18, 1979
INVENTOR(S) : Rowland G. Mowrey and Edwin N. Oftedahl It is certified that error appears in the above-identified patent and that said Letters Patent are hereby corrected as shown below:

Column 11, line 45, the formula reading

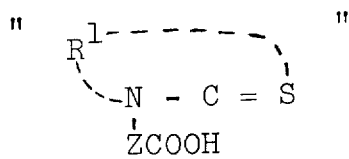  should read  

Column 15, line 67, that part of the formula reading "(3,6-Dioxoactane)" should read --- (3,6-Dioxaoctane) ---.

Column 18, line 49, "iodine" should read ---iodide---.

Signed and Sealed this

Ninth Day of December 1980

[SEAL]

Attest:

SIDNEY A. DIAMOND

Attesting Officer    Commissioner of Patents and Trademarks